United States Patent [19]

Hadcock et al.

[11] Patent Number: 5,065,630
[45] Date of Patent: Nov. 19, 1991

[54] INTEGRATED SYSTEM FOR AIRCRAFT CRACK DETECTION

[75] Inventors: Richard N. Hadcock, Huntington; Richard R. Chipman, Centerport; Michael Horn, South Setauket; Richard F. Chance, Bayport, all of N.Y.

[73] Assignee: Grumman Aerospace Corporation, Bethpage, N.Y.

[21] Appl. No.: 536,808

[22] Filed: Jun. 12, 1990

[51] Int. Cl.⁵ ............................................. G01M 5/00
[52] U.S. Cl. ..................................................... 73/802
[58] Field of Search ................. 73/577, 583, 587, 801, 73/802, 799

[56] References Cited

U.S. PATENT DOCUMENTS

| | | | |
|---|---|---|---|
| 2,340,505 | 2/1944 | Beed | 73/802 |
| 3,713,127 | 1/1973 | Keledy et al. | 340/261 |
| 3,824,377 | 7/1974 | Notvest | 235/92 PD |
| 3,883,879 | 5/1975 | Kettering | 33/25.3 |
| 3,911,733 | 10/1975 | Bhuta et al. | 73/802 |
| 3,956,731 | 5/1976 | Lewis, Jr. | 340/516 |
| 3,985,024 | 10/1976 | Horak | 73/71.4 |
| 4,010,708 | 3/1977 | Keledy et al. | 116/65 |
| 4,036,057 | 7/1977 | Morais | 73/88 |
| 4,136,568 | 1/1979 | Seymour | 73/655 |
| 4,453,413 | 6/1984 | Schneider | 73/802 |
| 4,808,814 | 2/1989 | Hofer et al. | 250/227.15 |

OTHER PUBLICATIONS

Bailey, "Acoustic Emission for In-Flight Monitoring on Aircraft Structures", Materials Evaluation, pp. 165-171.

Primary Examiner—Robert Raevis
Attorney, Agent, or Firm—Bacon & Thomas

[57] ABSTRACT

An automated system is disclosed for rapidly inspecting a complete aircraft and detecting cracks in the airframe. For inspecting the aircraft fuselage, the system incorporates a framework disposed over the fuselage and extending along a major portion of the length of the fuselage. Beams having suction devices and acoustic sensors are movably attached to the framework and are moved into a position adjacent to the outer surface of the fuselage when the aircraft has been located within the framework. The suction devices attach the beams to the fuselage surface along fuselage panel joints or other areas to be inspected. Several acoustic sensors, located on each beam, are connected to a device for analyzing and recording or visually displaying the signals generated by the sensors upon the detection of noise generated by the formation or propagation of cracks. In order to simulate the loads on the fuselage encountered during flight, the interior of the fuselage is pressurized via the aircraft engines or an external pressurization source. The system according to the invention may also be used to inspect the aircraft wings by placing inflatable bags beneath the wing and inflating them so as to exert upward loads on the wing. Additional inflatable bags are placed between the fuselage and a framework extending over the aircraft fuselage such that, when inflated, they exert downward loads on the upper surface of the aircraft fuselage. The fuselage is pressurized to prevent collapse. Mounting beams having acoustic sensors are attached via suction devices to the aircraft wing at joints, or other areas to be inspected.

22 Claims, 6 Drawing Sheets

INTEGRATED SYSTEM FOR AIRCRAFT CRACK DETECTION

BACKGROUND OF THE INVENTION

The present invention relates to a system for inspecting a completed air frame structure for cracks, more specifically such a system utilizing acoustic emission sensors to sense the formation or propagation of such cracks when the aircraft is subjected to force loading Today's commercial aircraft are remaining in service longer than ever before. Factors contributing to this increase in the service life of such aircraft are the quality of the design and construction of such aircraft, the ever increasing costs of new aircraft to replace the older aircraft and the higher level of cost monitoring of the commercial airlines. The older aircraft may be continually updated by modernizing the electronics and avionics, as well as replacing and updating the interior of the aircraft to make the older airframe competitive with newer aircraft.

Inevitably, however, the older airframes will become increasingly vulnerable to metal fatigue cracks as their service life increases. Such cracks are formed in the metal as a result of fatigue or corrosion in the metal. Metal fatigue may be generated by the forces to which the metal is subjected during numerous take offs and landings, while corrosion may be caused by exposure to a corrosive atmosphere, such as operating the aircraft near large bodies of salt water. If the developing cracks remain undetected and are allowed to increase in size, they may be sufficient to cause the metal to fail at stresses below the normal yield strength of the metal. Such failure is the result of the resulting concentration of localized stresses above the yield strength at the location of the crack in the material. The larger the crack, the greater is the likelihood of the catastrophic failure of the material In order to safely keep the older aircraft in operation, it is necessary to accurately inspect the entire airframe to detect and repair such cracks before they reach a level that could endanger the structural capability of the airframe. While it is known to use such inspection techniques as acoustic emission crack detection on individual aircraft components, such inspection techniques have not been applied efficiently to the entire airframe of a completed aircraft. The known inspection techniques typically require an acoustic emission sensor to be clamped or otherwise affixed onto the surface of the metal part being inspected, a requirement which would render the application of such sensors to the large surface area of a completed airframe time consuming and impractical.

While it would be possible to disassemble the aircraft and inspect each of its component parts, such an inspection technique would, quite obviously, be totally impractical on a commercial basis.

There is thus a need to provide an automated system for rapidly inspecting the completed major components of an aircraft airframe, such as the fuselage and wings, without requiring such elements to be disassembled.

SUMMARY OF THE INVENTION

A system is disclosed for detecting cracks in a completed aircraft airframe that does not require disassembling of any of the aircraft components. For inspecting the aircraft fuselage, the system incorporates a framework disposed over the fuselage and extending along a major portion of the length of the fuselage. Beams having suction devices and acoustic sensors are movably attached to the framework and are moved into a position adjacent to the outer surface of the fuselage when the aircraft has been located within the framework. The suction devices attach the beams to the fuselage surface along fuselage panel joints or other areas to be inspected. Several acoustic sensors are located on each beam and are connected to a device for analyzing and recording or visually displaying the signals generated by the sensors upon the detection of noise generated by the formation or propagation of cracks. In order to simulate the loads on the fuselage encountered during flight, the interior of the fuselage is pressurized via the normal aircraft pressurization system using the aircraft engines or from an outside source.

The system according to the invention may also be used to inspect the aircraft wings. In this instance, inflatable bags are placed beneath the wing and inflated so as to exert upward loads on the wing. Additional inflatable bags are placed between the fuselage and a framework extending over the aircraft fuselage such that, when inflated, they exert downward loads on the upper surface of the aircraft fuselage. In order to prevent possible buckling of the fuselage panels, the interior of the fuselage is pressurized using the aircraft pressurization system.

Mounting bars having acoustic sensors are attached via suction devices to the upper surface of the aircraft wing at panel joints, or other areas to be inspected. Again, these sensors are connected to a device for analyzing and recording or visually displaying signals generated by the sensors when a crack is detected.

DESCRIPTION OF THE PREFERRED EMBODIMENT

Figure 1:
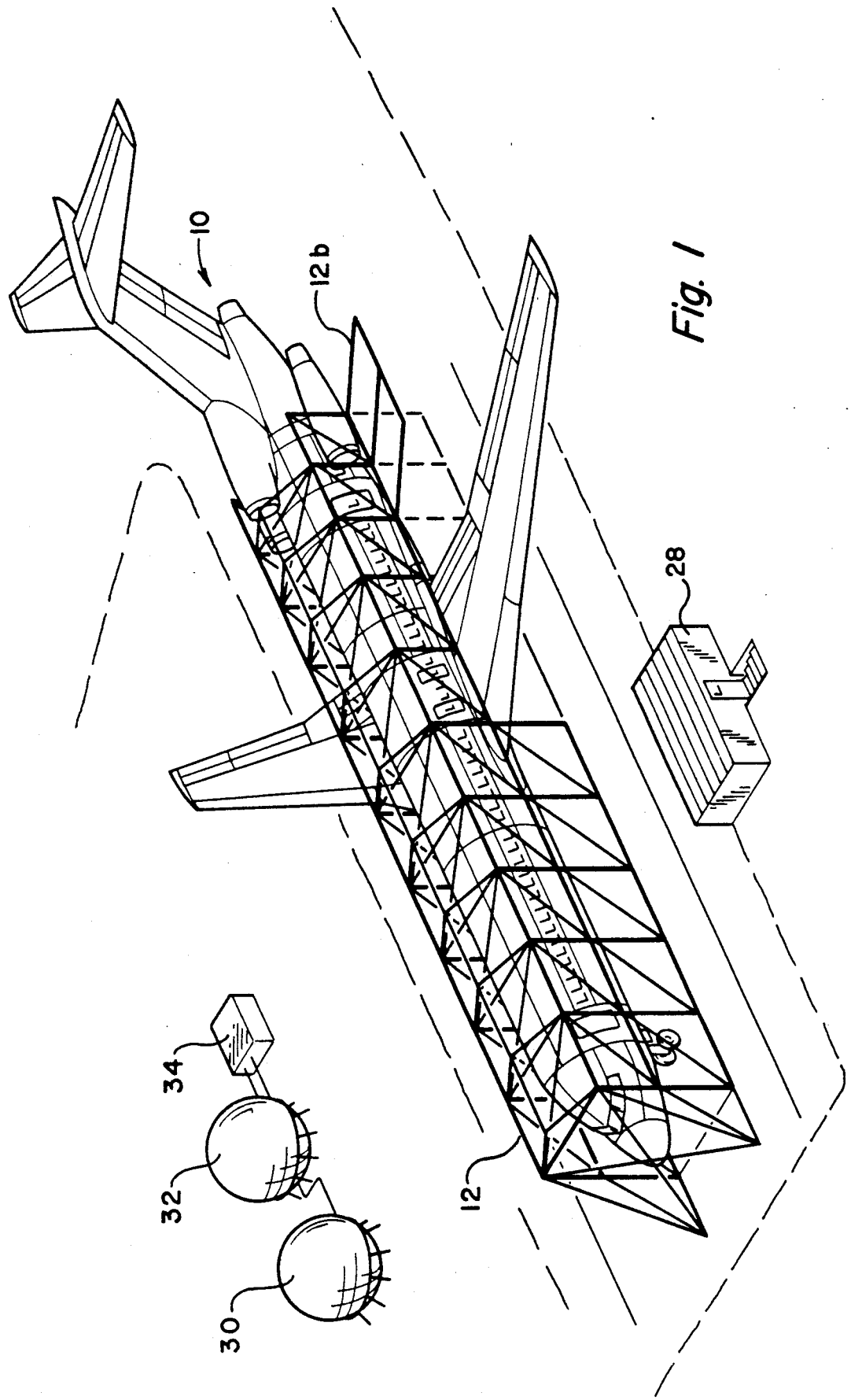
FIG. 1 is a perspective view of the system according to the invention utilized to inspect an aircraft fuselage.

The system according to the invention, as illustrated in FIG. 1, may be utilized to inspect the fuselage of aircraft 10 for cracks. The system includes a framework 12 extending over the fuselage of aircraft 10 and along a majority of the length of the fuselage. The framework 12 may be fabricated using structural members of any known configuration and may be a permanent or temporary installation. A rear portion, designated at 12b, of the framework may pivot upwardly to allow the wings of the aircraft 10 to pass as the aircraft is towed into position beneath the framework. Once in position, the sections 12b may be lowered, as indicated in dashed lines in FIG. 1 to conform to the remainder of the framework structure.

Figure 2:
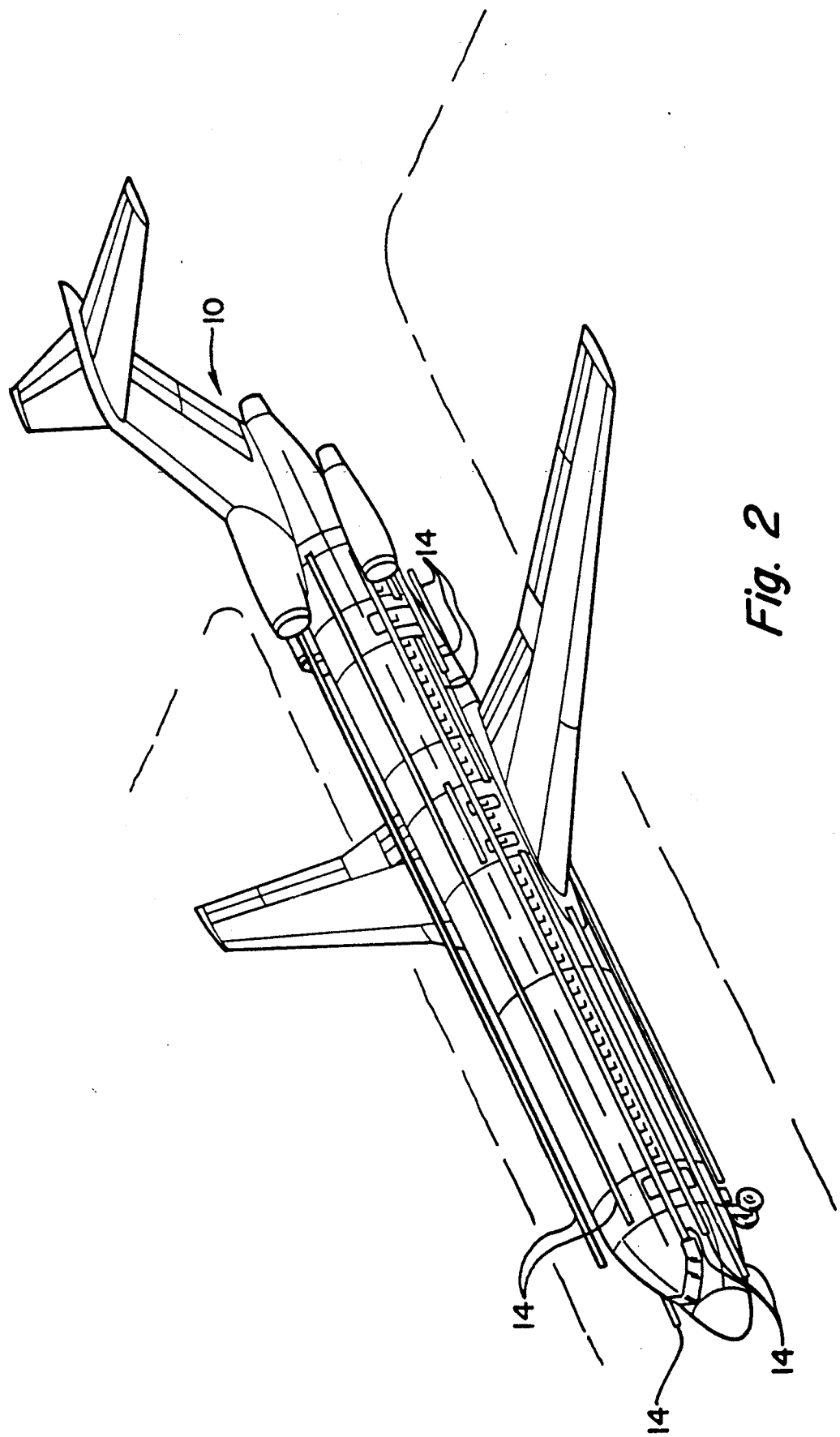
FIG. 2 is a perspective view, similar to FIG. 1, with the framework removed to illustrate the positions of the beams holding the acoustic sensors.

A plurality of beams 14 are movably attached to the framework 12 such that they are movable between a position in which the beam is located adjacent to the surface of the aircraft fuselage and a position in which the beams are displaced away from the fuselage. As the aircraft is being towed into or removed from the framework 12, the beams 14 are in their positions displaced away from the aircraft fuselage to provide clearance. The beams 14 are located around the fuselage so as to extend along joints between the fuselage panels, or to cover any other areas that may wish to be inspected. As illustrated in FIG. 2, the beams 14 may extend along the aircraft fuselage in a direction generally parallel to the longitudinal axis of the fuselage.

Figure 3:
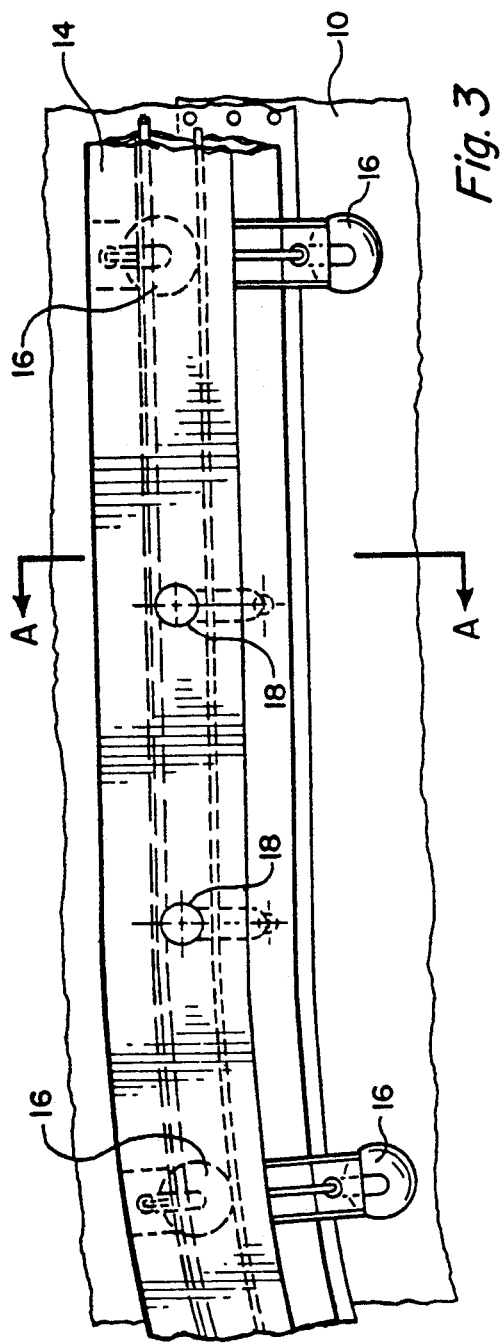
FIG. 3 is a partial, enlarged view of one of the sensor mounting beams illustrated in FIG. 2.
Figure 4:
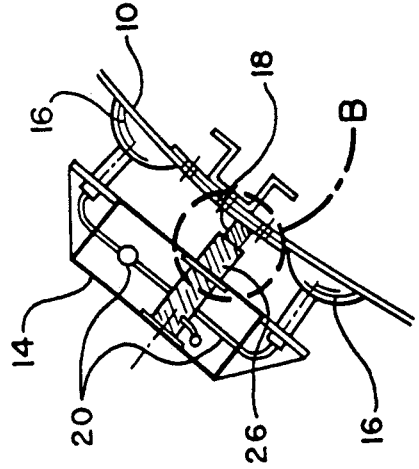
FIG. 4 is a cross-sectional view taken along line A—A of the sensor mounting beam shown in FIG. 3.
Figure 5:
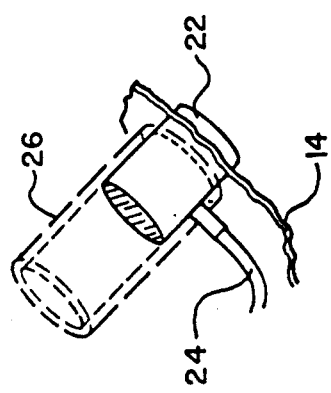
FIG. 5 is an enlarged, perspective view of one of the acoustic sensors shown in circle B in FIG. 4.

As can be seen in FIG. 3, each of the beams 14 has a plurality of suction devices 16 attached thereto, as well as a plurality of acoustic sensors 18. When the beams 14 are moved into their positions adjacent to the aircraft fuselage, the suction devices 16 are brought into contact with the fuselage surface. The suction devices 16 may have a flexible rubber cup coming into contact with the fuselage surface and be connected, via conduits 20 to a known vacuum source. The vacuum source reduces the air pressure within the cups of the suction devices 16 in order to affix the beams 14 to the fuselage surface.

The acoustic sensors 18, which may be of any known acoustic emission type sensor, comprises a transducer 22 attached to a data analyzing and recording system via conduit 24 in a known fashion. The transducer 22 may be attached to the beam 14 via an elongated cylinder 26 and may be moved into and out of contact with the fuselage surface via any known means such as pneumatic pressure or an electromagnetic device. As is well known in the art, such device may move the transducer 22 into contact with the fuselage surface such that the sensor 18 may generate an output signal upon sensing the acoustic emissions from the formation of a crack or the propagation of the crack. The material undergoing fracture produces a wave-like propagation of released strain energy which are also known as acoustic waves. In the formation of cracks, it is known that the crack grows in discrete steps rather than in a continuous fashion. At each incremental crack growth, acoustic energy is released and propagated in the material.

Means are provided on the beams, such as spray nozzles, to deposit either a liquid coupling medium or a dry coupling medium between the fuselage surface and the transducer 22. Such liquid or dry coupling medium enables the transducers 22 to attain acoustic coupling to the fuselage surface.

Each of the sensors 18 is connected to a system for recording and analyzing the output signals of the sensors. The connection between the sensors and the recorder/analyzer system may use electrical wires or fiber optic cables.

Figure 10:
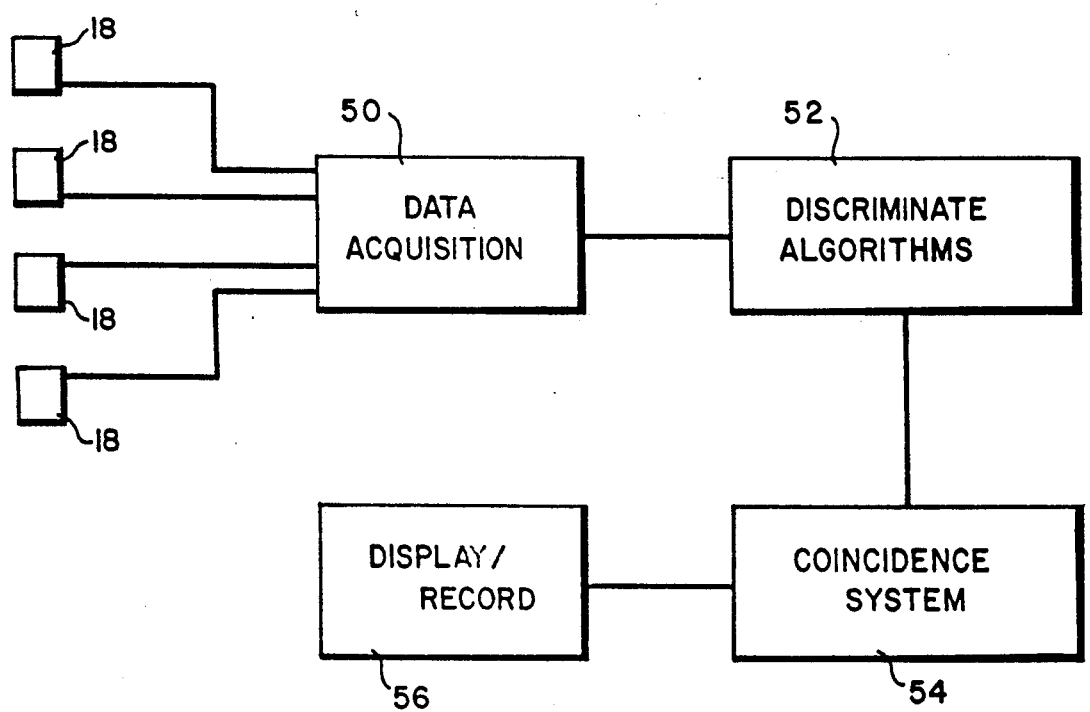
FIG. 10 is a schematic diagram of the system to analyze and display the data accumulated by the acoustic sensors.

It is envisioned that a system such as illustrated in FIG. 10 may be utilized to analyze and display/record the sensor signals. This system may comprise a data acquisition system 50 receiving signals generated from sensors 18, a discriminating algorithm means 52, a coincidence system 54 to generate a t time of arrival between transducer signals and a display/recorder system 56. Known systems, such as that set forth in U.S. Pat. No. 3,985,024 to Horak as well as the Spartan 3000 system made by Physical Acoustic Corp. of Lawrenceville, N.J. may be used to analyze and display/record the signals generated by the sensors 18.

The recorder/analyzer system- may be located in the control center 28 located adjacent to the framework 12 as illustrated in FIG. 1. The test facility may also comprise compressed air storage tanks 30 and 32 as well as air compressors located in building 34 for providing compressed air. The compressed air from tanks 30 and 32 are connected to the framework 12 in known fashion and may be utilized to move the beams 14 between their adjacent and displaced positions, as well as to move the transducers 22 of the acoustic sensors 18 into and out of contact with the fuselage surface. Alternatively, these operations may be performed using electro-mechanical systems. The compressed air may also be connected with the aircraft's pressurization system instead of the aircraft engines in order to pressurize the interior of the aircraft fuselage to simulate normal flight conditions. The interior of the fuselage is pressurized during the testing procedure in order to place the fuselage structure under stress.

The system according to the invention may also be used to inspect the aircraft wings for any cracks. As illustrated in FIGS. 6-9, inflatable bag members 36 are placed beneath the wings 38 of the aircraft 10. The inflatable bag member 36 may be segmented and the individual segments individually inflated in order to vary the loads placed upon the wing 38. The inflatable bag member 36 is located such that, as it is inflated and expands, it contacts the undersurface of the wing 38 so as to exert upward loads thereon. It has been found that simulated 2.0 g flight loads may be imposed upon the wing by inflating the bag members to a pressure of approximately 1.8 psi.

Sets of sensor mounting beams 14 are located on the upper and lower surfaces of the wing structure 38 at locations at which it is desired to inspect for cracks. such as wing panel joints, flap tracks, landing gear support structure, etc. The mounting beams 14 are attached to the desired area via suction cups and suction devices similar to that shown in FIG. 3. The suction devices may be attached to a known vacuum source and attached to the desired wing location. Each of the mounting beams also has a plurality of acoustic sensors mounted thereon which may be movable into contact with the wing structure. Each of the sensors are connected to the recorder/analyzer system via electrical wires or fiber optic cables 40.

Figure 6:
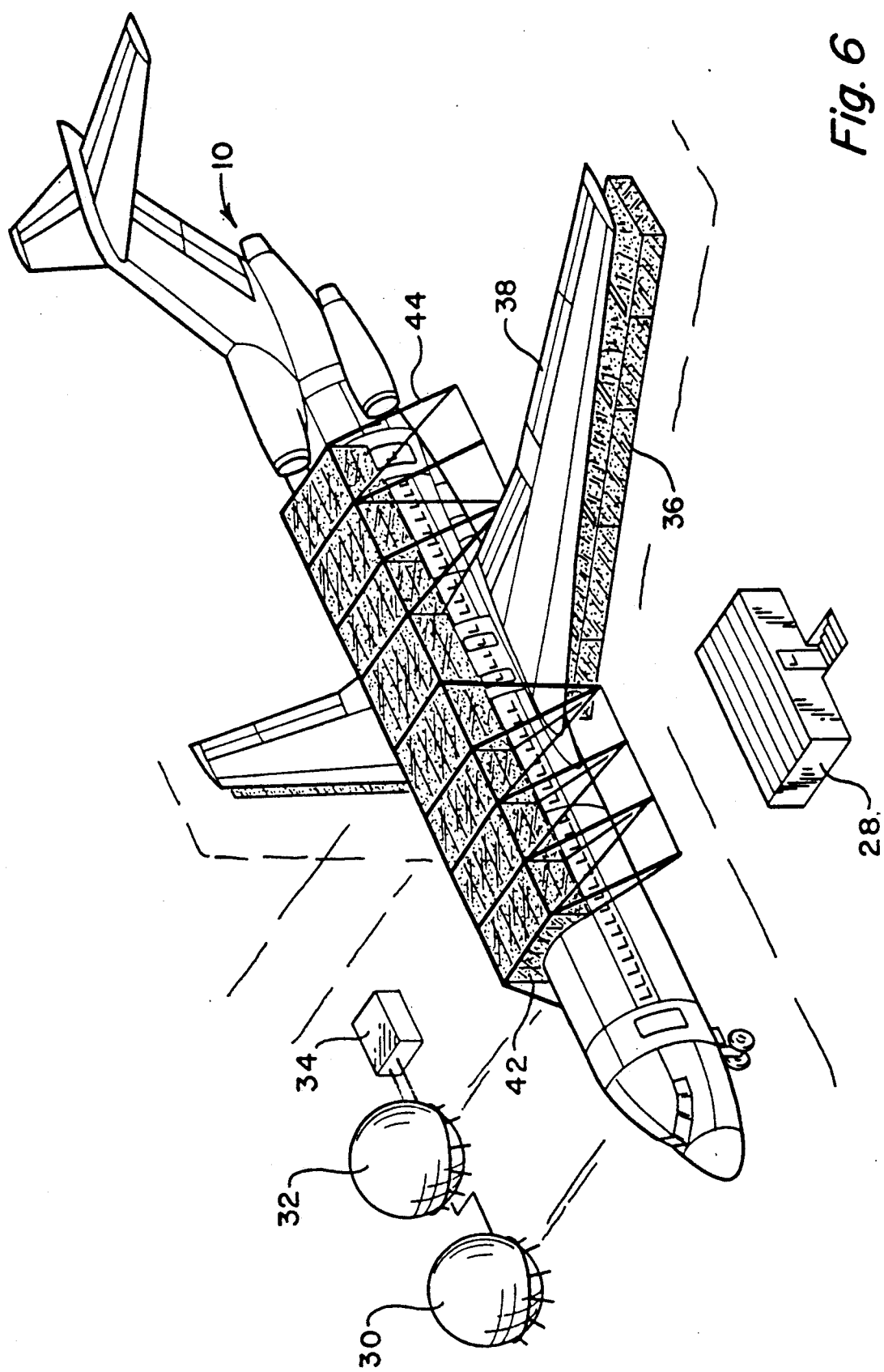
FIG. 6 is a perspective view of the system according to the invention utilized to inspect the aircraft wings.
Figure 7:
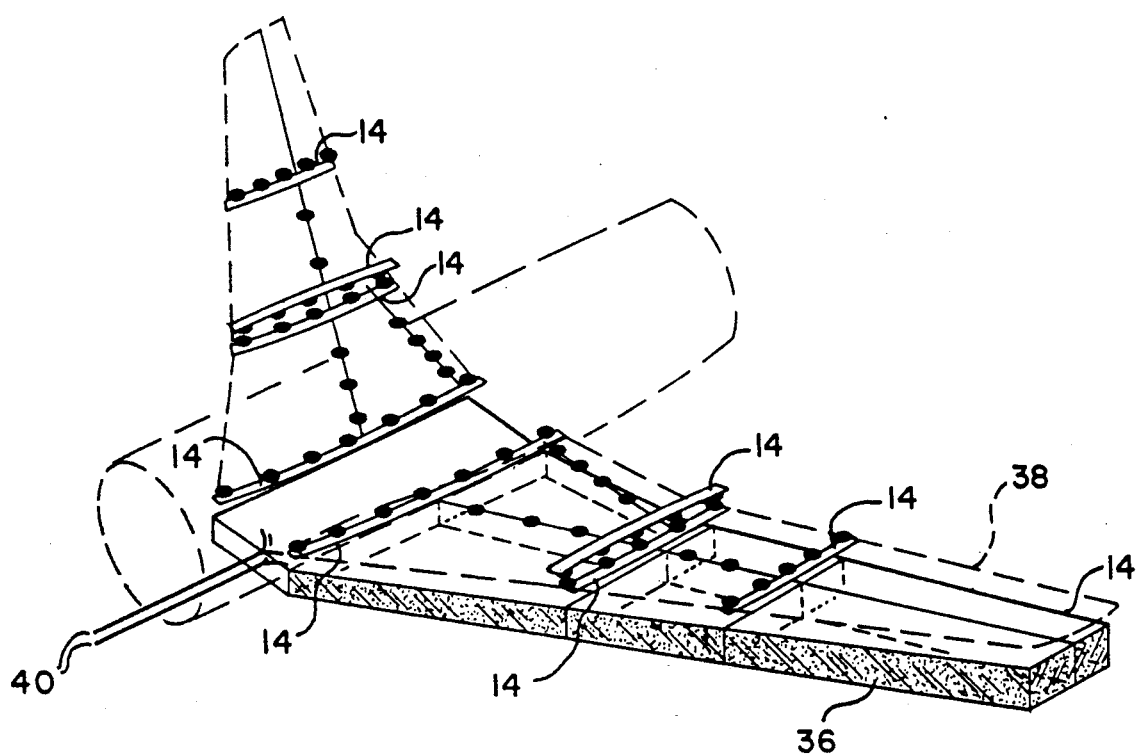
FIG. 7 is a partial view illustrating the location of the inflatable bags and the mounting beams on the aircraft wings.

Additional inflatable air bag members 42 are interposed between a framework 44 and the aircraft fuselage. These air bag members may be pressurized to approximately 2.5 psi and, when so inflated, bear against an upper surface of the aircraft fuselage to exert downward loads thereon so as to balance the wing loads. The interior of the fuselage may be pressurized to preclude collapse of the fuselage structure. As illustrated in FIG. 6, the framework 44 may extend over the fuselage a distance both fore and aft of the wing/fuselage juncture.

Figure 8:
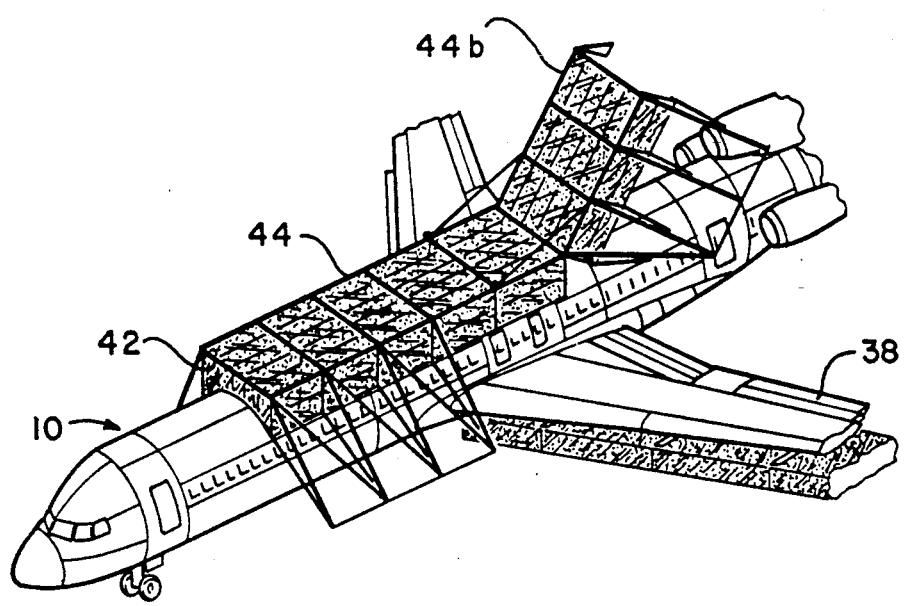
FIG. 8 is a partial, perspective view illustrating the fuselage framework and the inflatable bags shown in FIG. 6.
Figure 9:
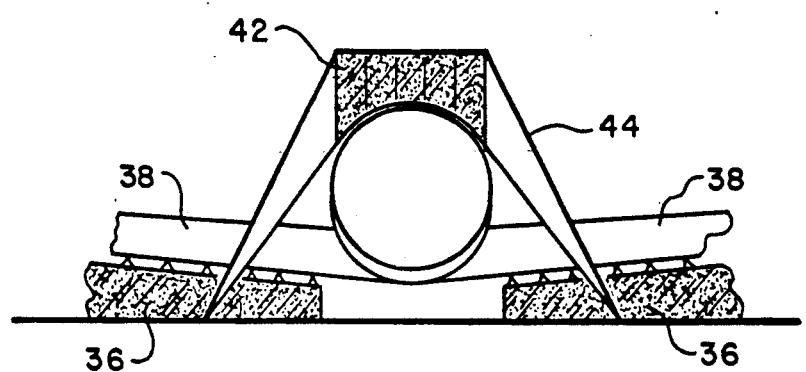
FIG. 9 is a partial, cross sectional view of the fuselage and wings of the aircraft illustrating the relative positions of the inflatable bags.

As illustrated in FIG. 8, the rear portion 44b of the framework 44 may pivot upwardly to allow the aircraft 10 to be towed into position beneath the framework. Once the aircraft is properly located, the rear portion 44b is lowered to the position shown in FIG. 6 prior to inflation of the inflatable bag members 42.

Although the system according to the invention has been described in terms of using acoustic emission sensors, it is quite possible to use other types of sensors without exceeding the scope of this invention. Any other type of non-destructive inspection sensors and equipment can be attached to the sensor mounting beams and used to inspect the aircraft airframe for cracks. Such known equipment may include:

a) Magneto-Optic/Eddy Current Imagers (ECI) are known and may be used to detect surface cracks through the painted structure of an aircraft. In order to utilize this type of sensor with the invention, rails may be attached to the sensor mounting beams and the magneto-optic/eddy current imagers mounted on the rail with an electric drive motor to move them along the rail to the positions required by the system operator. Data from the magneto-optic/eddy current imagers provide a video image which is used by the operator to remotely control the ECI sensor and examine the structure for cracks. At the same time, the data may be stored and analyzed utilizing an automated recognition system.

b) Acousto-Ultrasound (AU) is used to identify structural disbonds and weak bonds in fuselage joints. An exciter vibrates the structure ultrasonically and a transducer detects and records emissions. The combined exciter/transducer system may be enclosed in a rubber tired wheel which rides along the same rail as that described above for the ECI system. The position of the acousto-ultrasound wheel may be controlled by the operator using a video camera. The data is recorded and analyzed in a manner similar to that described above for the ECI system.

c) Thermography is an optical imaging system to detect the presence of corrosion in aluminum-alloy skins and disbonds in fuselage bonded joints. An infrared (IR) video camera and an associated heating device may be mounted on the rail, and positioned by the operator using the video image. The data, which is in the form of temperature contours, may be analyzed by the operator or may be recorded and analyzed by the automated recognition system (ARS).

d) Shearography and holography use laser image systems which can detect minute surface displacement caused by structural or thermal distortion. Again, the known equipment can be mounted on the rail and operated in a manner similar to those described above.

The non-destructive detection techniques set forth in a), b) and c) above do not require the aircraft to be force loaded.

The foregoing description is provided for illustrative purposes only and should not be construed as in any way limiting this invention, the scope of which is defined solely by the appended claims.

What is claimed is:

1. A method for detecting cracks in a completed aircraft on the ground wherein the aircraft has a fuselage and a wing comprising the steps of:
   a) placing the completed aircraft within a framework such that the framework extends over a majority of the length of the fuselage;
   b) mounting a plurality of sensors on the framework such that they are movable between positions in contact with and displaced away from an outer surface of the fuselage;
   c) placing the plurality of sensors in operative position with respect to a surface of the aircraft to be tested, the sensors having means to generate a signal upon detecting a crack in the aircraft airframe;
   d) applying loads to the aircraft simulating the loads encountered by the aircraft during flight; and,
   e) analyzing signals generated by the plurality of sensors during the application of the loads to detect and locate any cracks in the airframe under test.

2. The method according to claim 1 wherein the loads are applied by pressurizing the interior of the fuselage.

3. The method according to claim 1, wherein the mounting of the plurality of sensors on the framework comprises the steps of:
   a) movably attaching a plurality of beams to the framework such that the beams extend generally parallel to a longitudinal axis of the fuselage and are movable between positions in contact with and displaced from the fuselage;
   b) mounting a plurality of suction devices on each of the beams such that the suction devices contact an exterior surface of the fuselage when the beams are in position adjacent to the fuselage;
   c) attaching at least one sensor to each beam; and,
   d) placing the sensor in contact with the exterior surface of the fuselage.

4. The method according to claim 1 wherein the sensors are acoustic emission sensors which generate an output signal upon sensing the noise generated by the formation or propagation of a crack.

5. The method according to claim 1 comprising the further steps of:
   a) mounting the sensors on at least one mounting beam; and,
   b) attaching the at least one mounting beam to a surface of the wing.

6. The method according to claim 5 comprising the additional steps of mounting suction devices on the at least one mounting beam to hold the at least one mounting beam on the wing surface.

7. The method according to claim 5 wherein the load is applied by the steps of:
   a) placing at least one first inflatable bag member beneath the wing; and,
   b) inflating the first bag member such that it contacts a lower surface of the wing and exerts upward loads on the wing.

8. The method according to claim 7 comprising the additional steps of:
   a) placing at least one second inflatable bag member between the framework and an upper portion of the fuselage; and,
   b) inflating the second bag member so as to contact the framework and the upper portion of the fuselage so as to exert downward loads on the fuselage.

9. The method according to claim 8 comprising the additional step of pressurizing the interior of the fuselage.

10. A system for detecting cracks in a completed aircraft on the ground wherein the aircraft has a fuselage and a wing comprising:
    a) a framework disposed about the fuselage and extending over a majority of the length of the fuselage;
    b) support means supporting a plurality of sensors in operative position with respect to a surface of the aircraft to be tested, the sensors having means to generate a signal upon detecting a crack in the aircraft, the support means comprising:
  i) at least one mounting beams;
  ii) mounting means to mount the plurality of sensors on the at least on mounting beam; and,
  iii) attaching means to attach the at least one mounting beam to a surface of the wing;
c) means for applying loads to the aircraft simulating the loads encountered by the aircraft during flight comprising at least one first inflatable bag member located beneath the wing such that, when the at least one bag member is inflated it contacts a lower surface of the wing to exert upward loads thereon;
d) at least one second inflatable bag member located between the support framework and an upper portion of the fuselage such that, when the at least one second bag member is inflated, it exerts downward loads on the fuselage; and,
e) means to analyze the signals generated by the sensors during the application of the loads to detect any crack in the aircraft.

11. The system according to claim 11 wherein the mounting means comprises means to mount the plurality of sensors on the framework such that they are movable between positions adjacent to and displaced from an outer surface of the fuselage.

12. The system according to claim 11 wherein the means to apply the loads further comprises means to pressurize the interior of the fuselage.

13. The system according to claim 11 wherein the support means further comprises:
  a) a plurality of beams;
  b) attaching means attaching the plurality of beams to the framework such that they are movable between positions adjacent to and displaced away from the fuselage;
  c) a plurality of suction devices mounted on each beam such that the suction devices contact an exterior surface of the fuselage when the beams are in their position adjacent to the fuselage; and,
  d) means to mount at least one sensor to each beam.

14. The system according to claim 10 wherein the sensors are acoustic emission sensors which generate an output signal upon sensing the noise generated by the formation, propagation or presence of a crack.

15. The system according to claim 10 wherein the attaching means comprises suction devices mounted on the at least one mounting beam.

16. The system according to claim 10 further comprising means to pressurize the interior of the fuselage.

17. A method for detecting cracks in a completed aircraft on the ground wherein the aircraft has a fuselage and a wing comprising the steps of:
  a) placing the completed aircraft within a framework such that the framework extends over a majority of the length of the fuselage;
  b) placing a plurality of sensors in operative position with respect to a surface of the aircraft to be tested, the sensors having means to generate a signal upon detecting a crack in the aircraft airframe by the steps of:
    i) mounting the sensors on at least one mounting beam: and,
    ii) attaching the at least one mounting beam to a surface of the wing;
  c) applying loads to the aircraft simulating the loads encountered by the aircraft during flight by the steps of:
    i) placing at least one first inflatable bag member beneath the wing; and,
    ii) inflating the first bag member such that it contacts a lower surface of the wing and exerts upward loads on the wing;
  d) placing at least one second inflatable bag member between the framework and an upper portion of the fuselage;
  e) inflating the second bag member so as to contact the framework and the upper portion of the fuselage so as to exert downward loads on the fuselage; and,
  f) analyzing signals generated by the plurality of sensors during the application of the loads to detect and locate any cracks in the airframe under test.

18. The method according to claim 17 comprising the additional step of mounting the plurality of sensors on the at least one mounting beam such that they are movable between positions in contact with and displaced away from an outer surface of the fuselage.

19. The method according to claim 17 comprising the additional steps of pressurizing the interior of the fuselage when applying loads to the aircraft.

20. The method according to claim 17 wherein the placing of the plurality of sensors in operative position comprises the additional steps of:
  a) movably attaching a plurality of beams to the framework such that the beams extend generally parallel to a longitudinal axis of the fuselage and are movable between positions in contact with and displaced from the fuselage;
  b) mounting a plurality of suction devices on each of the beams such that the suction devices contact an exterior surface of the fuselage when the beams are in position adjacent to the fuselage;
  c) attaching at least one sensor to each beam; and,
  d) placing the sensor in contact with the exterior surface of the fuselage.

21. The method according to claim 17 wherein the sensors are acoustic emission sensors which generate an output signal upon sensing the noise generated by the formation or propagation of a crack.

22. The method according to claim 17 comprising the additional steps of mounting suction devices on the at least one mounting suction devices on the at least one mounting beam to hold the at least one mounting beam on the wing surface.

* * * * *